United States Patent [19]

Cavoto et al.

[11] Patent Number: 4,904,168
[45] Date of Patent: Feb. 27, 1990

[54] CASSETTE ASSEMBLY FOR OPHTHALMIC SURGERY SYSTEM

[75] Inventors: Robert Cavoto, Hauppauge; Anthony DiGiacomo, Babylon; Christopher V. Kayser, Bay Shore; Joseph D. Spinosa, Wantagh, all of N.Y.

[73] Assignee: United Sonics, Inc., Hauppauge, N.Y.

[21] Appl. No.: 291,947

[22] Filed: Dec. 28, 1988

[51] Int. Cl.⁴ ............................................. F04B 43/12
[52] U.S. Cl. ..................................... 417/477; 417/475
[58] Field of Search ................. 417/474, 475, 476, 477

[56] References Cited

U.S. PATENT DOCUMENTS

| | | | |
|---|---|---|---|
| 4,187,057 | 2/1980 | Xanthopoulous | 417/63 |
| 4,483,666 | 11/1984 | Schubert et al. | 417/475 X |
| 4,493,695 | 1/1985 | Cook | 604/27 |
| 4,537,561 | 8/1985 | Xanthopoulous | 417/63 |
| 4,626,648 | 12/1986 | Scheller | 604/319 |
| 4,627,833 | 12/1986 | Cook | 604/34 |
| 4,705,464 | 11/1987 | Arimond | 417/477 |
| 4,708,604 | 11/1987 | Kidera | 417/477 |
| 4,713,051 | 12/1987 | Steppe et al. | 604/30 |
| 4,735,558 | 4/1988 | Kienholz et al. | 417/477 |
| 4,798,580 | 1/1989 | De Meo et al. | 417/476 X |
| 4,813,855 | 3/1989 | Leveen et al. | 417/477 |

Primary Examiner—Donald E. Stout
Assistant Examiner—Eugene L. Szczecina, Jr.
Attorney, Agent, or Firm—Hoffmann & Baron

[57] ABSTRACT

A cassette and a cassette receptacle assembly are provided for use in an ocular surgical system. The cassette includes a housing which defines an arcuate race. A flexible tube extends across the race and conveys a fluid when compressed by the rollers of a roller pump. A slot is defined by the housing at the point where the tube forms a bend prior to entering the race. The slot has a height which is preferably smaller than the diameter of the tube and therefore prevents the tube from flattening as the rollers urge it away from the slot. The cassette mounting assembly includes a pair of cams which urge the cassette into a locked position with respect to the roller pump.

15 Claims, 4 Drawing Sheets

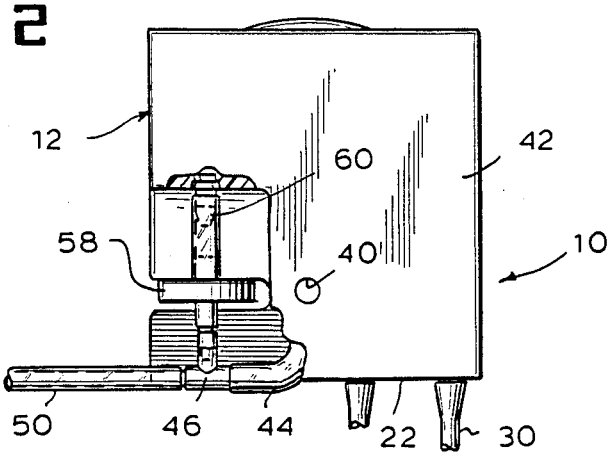
Fig. 2
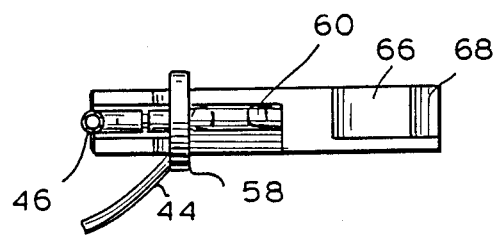
Fig. 3
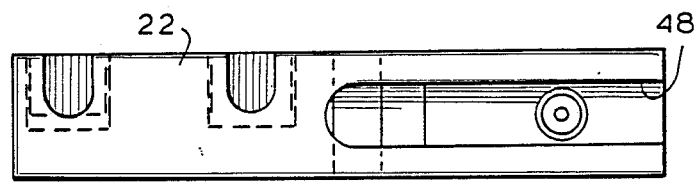
Fig. 4
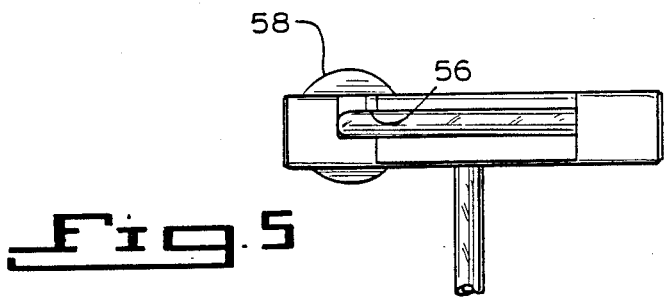
Fig. 5
Fig. 6
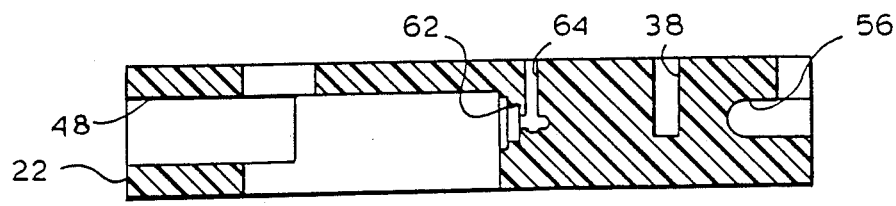

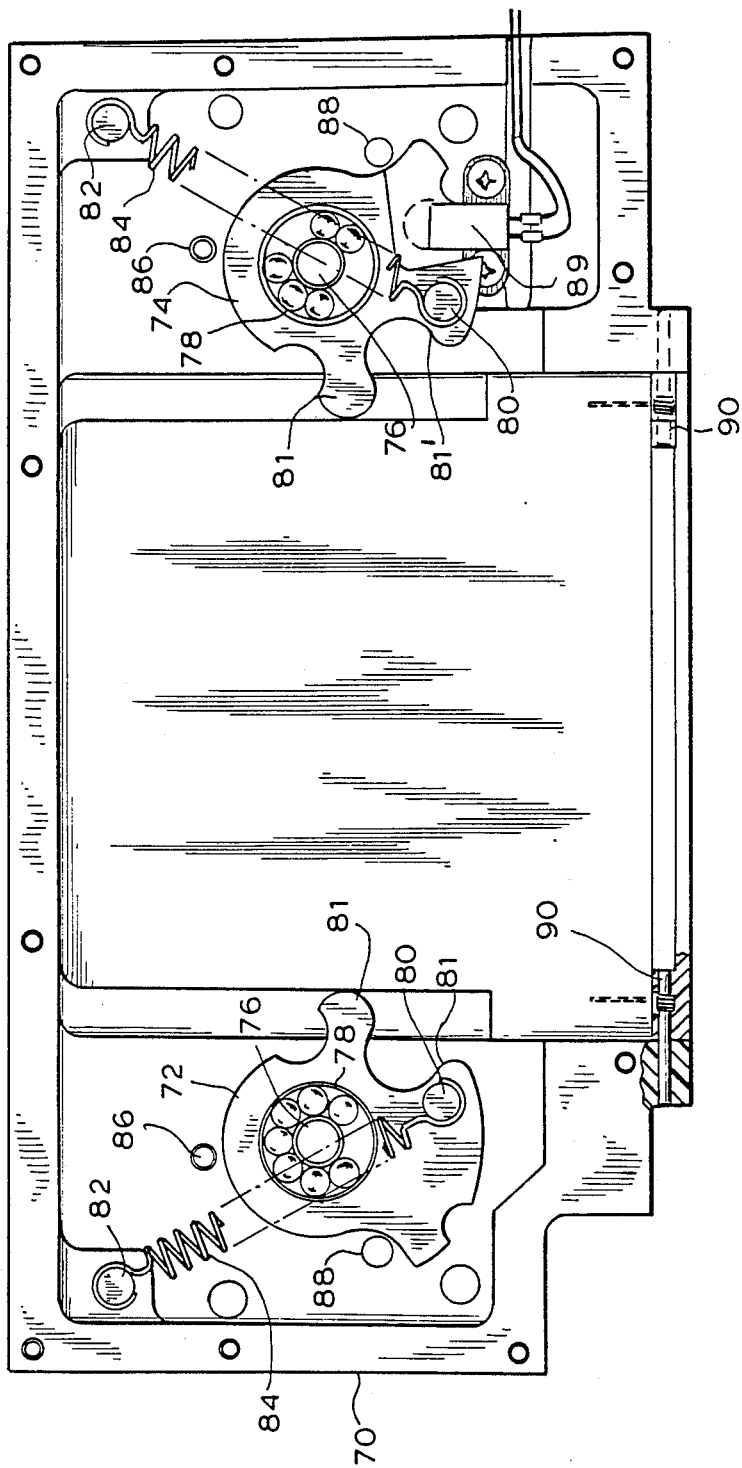

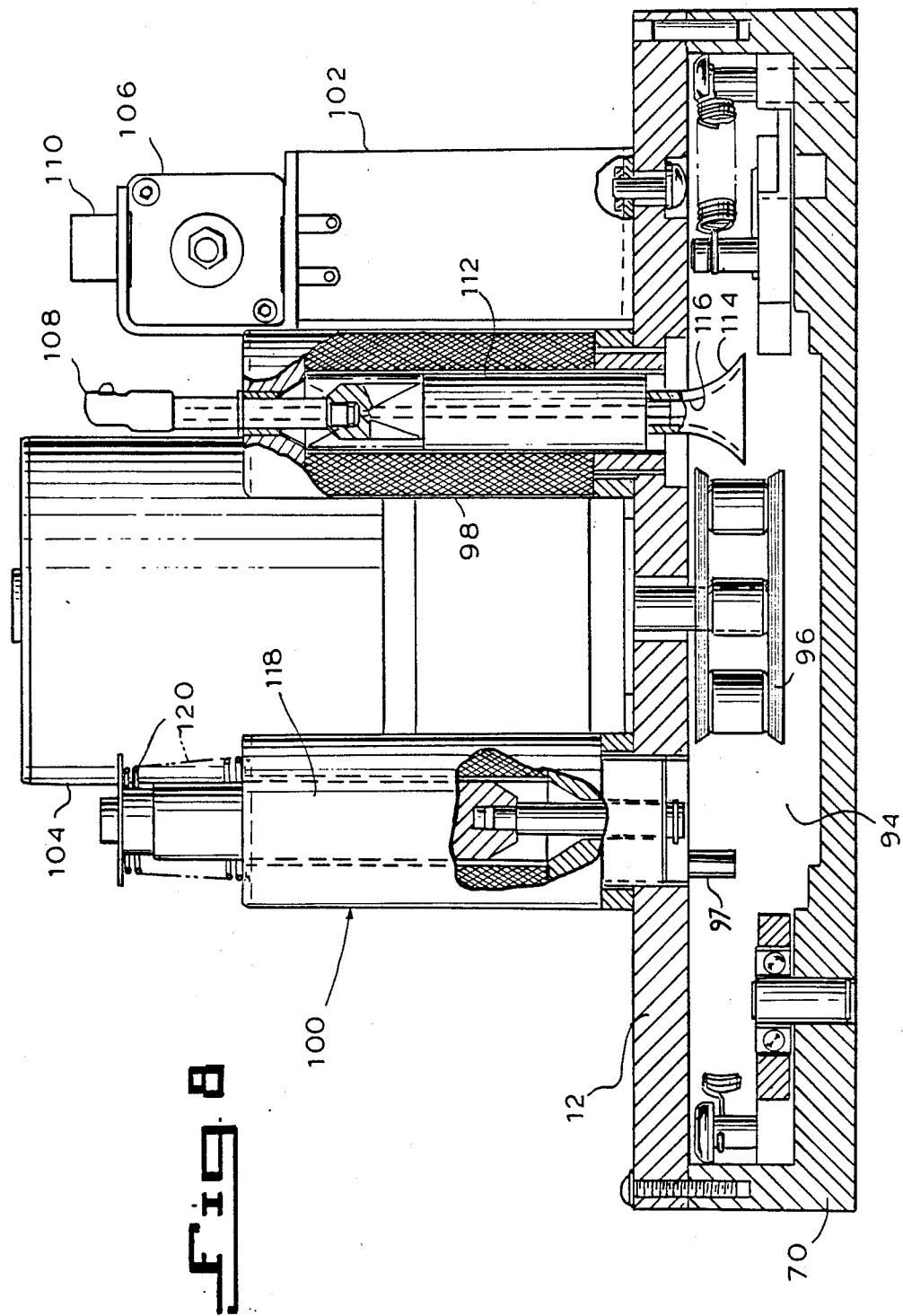

CASSETTE ASSEMBLY FOR OPHTHALMIC SURGERY SYSTEM

BACKGROUND OF THE INVENTION

The field of the invention relates to microsurgical equipment, and particularly to apparatus for providing irrigation to a surgical situs and aspiration for removing tissue and fluid therefrom.

Microsurgical systems are used for performing many operations today, including ophthalmic surgery. Systems for removing cataracts, for example, typically include a cutting probe and associated aspiration device for removing mascerated tissue to a collection vessel. An irrigation supply is also provided to replace the fluid removed through aspiration. The cutting probe and associated irrigation/aspiration lines are often mounted to the same handpiece which is in turn connected to a machine for controlling the cutting (or emulsifying), aspiration and irrigation procedures. Such machines include irrigation/aspiration manifolds including a roller pump and vacuum source for controlling aspiration, and valve means for controlling irrigation.

The irrigation/aspiration manifolds of most modern systems include disposable cassettes which maintain the irrigation and aspiration tubing in the desired positions with respect to the machine. U.S. Pat. Nos. 4,493,695, 4,626,248, 4,627,833, 4,713,051 and 4,735,558 disclose various cassettes and mounting assemblies therefor which have been proposed for use in ophthalmic surgery systems.

One of the problems encountered in the use of some cassettes is the unintentional pinching of the flexible aspiration tube as the roller pump operates. The roller pump includes a plurality of rollers which are rotated about an axis and bear against the tube. In addition to the desired occlusion of the tube between the rollers and a selected portion of the cassette manifold, the tube tends to be pulled in the direction of rotation of the pump rollers. The tube may accordingly become partially or completely occluded at the point where it is pulled against the manifold.

Another difficulty with respect to cassettes is in mounting them to the emulsifier/aspirator unit. Such units typically include horizontally disposed slots for receiving the cassettes. Latch mechanisms are provided for maintaining the cassette in the desired position with respect to the pump rollers, vacuum source and irrigation control means. Some cassette receptacles require the user to push the cassette into the correct position within the slot. This can sometimes result in improper seating if the proper force is not applied.

Another type of latching mechanism includes a pair of spring-loaded cams which resiliently urge the cassette towards the pump rollers. The cassette will accordingly tend to oscillate within the slot when the roller pump is actuated.

SUMMARY OF THE INVENTION

It is an object of the invention to provide a cassette assembly for an ophthalmic surgery system which allows the reliable operation thereof.

It is another object of the invention to provide a cassette having means for preventing the occlusion of a tube mounted thereon except where the tube contacts a pump roller.

In accordance with the above and other objects of the invention, a cassette and a cassette receptacle assembly are provided for use in an ocular surgical system. The cassette according to the invention includes an arcuate race. One end of the race includes a slot therein for receiving a flexible tube. The slot exerts pressure in the vertical direction upon the tube. If the pump rollers tend to pull the tube as they move away from the slot, the upper and lower walls of the slot prevent the tube from flattening against the inner, vertical slot surface. The tube is accordingly maintained in the open position at this point to allow proper aspiration of the surgical situs.

The cassette is locked into position by a pair of opposing, spring-loaded cams which engage the cassette upon insertion and thereupon automatically move and lock it into proper position. The cassette remains stationary when locked in position, even during the operation of the roller pump which causes the pump rollers to exert a force against the cassette. In addition, means are provided for maintaining the cassette at a fixed distance from the pump rollers. This fixed distance is crucial for maintaining the desired aspiration rate.

BRIEF DESCRIPTION OF THE DRAWINGS

FIG. 2 is a partially sectional bottom plan view thereof;

FIG. 3 is a side elevation view thereof;

FIG. 4 is an enlarged front elevation view thereof;

FIG. 5 is a rear elevation view thereof;

FIG. 6 is a sectional view thereof taken along line 6—6 of FIG. 1;

FIG. 7 is a partially sectional top plan view of a bottom portion of a cassette receptacle assembly; and FIG. 8 is a sectional side elevation view of a cassette receptacle assembly.

DETAILED DESCRIPTION OF THE INVENTION

Figure 1:
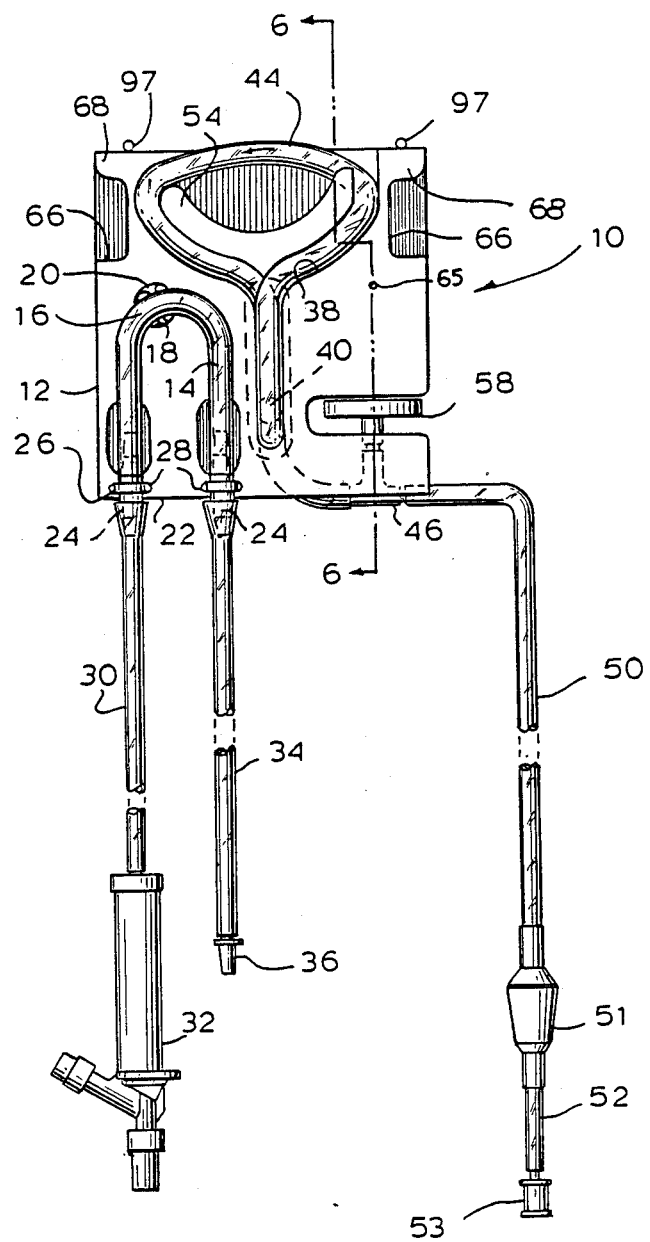
FIG. 1 is a top plan view of a cassette according to the invention.

A disposable or reusable cassette 10 for use in irrigation/aspiration systems is shown in FIGS. 1-6. The cassette 10 includes an integral plastic housing 12 having specifically designed channels, openings and passages to accommodate various tubes, fittings, and a hydrophobic filter.

Referring to FIG. 1, a U-shaped channel 14 is defined within the upper surface of the plastic housing 12 for receiving a flexible irrigation tube 16. The channel extends through a circular notch 18, the bottom of the notch including a narrow ridge 20 passing through the center thereof and running substantially perpendicular to the tube 16. The ridge facilitates the pinching of the tube when a plunger is inserted within the notch 18.

Each end of the U-shaped channel 14 opens into the front face 22 of the housing 12. A pair of plastic fittings 24 are secured to the housing walls defining the channel openings by an adhesive. Each fitting also includes an annular ring 26 which projects partially within a pair of lobes 28 extending laterally from the end portions of the channel to provide a mechanical retention. A first flexible tube 30 extends between one of the fittings and an IV bottle (not shown). An IV connector 32 is secured to the end of this tube. A second tube 34 is connected between the other of the two fittings 24 and a tapered male fitting 36. This tube supplies irrigation fluid from the IV bottle to the patient.

A second, generally Y-shaped channel 38 is defined within the upper surface of the cassette housing. A cylindrical passage 40 extends between the bottom surface of this channel and the bottom surface 42 of the cassette housing. An aspiration tube 44 is positioned within the channel, one end of which extends through the hole 40 and to a drainage bag or other waste receptacle (not shown). The other end is connected to one part of a tee 46 positioned in a slotted opening 48 adjoining the front face 22 of the housing. This arrangement is shown in FIGS. 2 and 4, the tube and tee being omitted in FIG. 4. A second aspiration tube 50 is connected between the opposite port of the tee 46 and a pinch bulb 51. A third aspiration tube 52 is connected between the pinch bulb and a tapered female fitting 53.

An arcuate race 54 is defined by the upper rear surface of the cassette housing. A slot 56, as shown most clearly in FIGS. 5 and 6, is defined by the housing walls at the inlet side of the race. The depth of the slot is slightly larger than as the diameter of the aspiration tube 44 while the height thereof is slightly less than said diameter to provide strain relief.

Referring to FIGS. 1-3 and 6, the tee 46 includes a third port which is connected to a hydrophobic filter 58. The filter is connected to a fitting 60 secured within a horizontal cylindrical passage 62 within the cassette housing. This passage adjoins a vertically extending passage 64 which terminates at an opening 65 in the upper surface of the housing 12.

Each side of the housing 12 includes a pair of opposing indentations 66 as shown in FIGS. 1 and 3. Each indentation is defined in part by a laterally extending flange 68 having an arcuate front and side surfaces.

FIG. 7 illustrates a bottom housing 70 of an irrigation/aspiration system prior to insertion of a cassette. A pair of cams 72, 74 are mounted to the bottom housing by a pair of shafts 76 and bearing assemblies 78, respectively. Each cam includes a vertically extending pin 80 mounted thereto and a finger 81 projecting therefrom. A second pair of vertically extending pins 82 are mounted to the bottom housing. A pair of coil springs 84 are connected to the respective pairs of pins 80, 82 and are maintained under tension thereby. A first pair of stop pins 86 are provided for restricting the rotation of the cams 72, 74 in a first direction. A second pair of stop pins 88 prevents the cams from rotating beyond a selected arc in a second rotational direction. A phototransistor 89 is mounted near one of the cams and detects when a cassette is inserted within the unit. Unless the cam is fully rotated to insure the cassette is in the proper operative position, the phototransistor will not allow the system to be operated. A pair of opposing, pins 90 are mounted near the front end of the bottom housing. These pins are operatively connected to a spring-loaded door (not shown) which automatically closes the slot once the cassette is removed therefrom.

FIG. 8 shows the bottom housing 70 mounted to a top housing 92, and a slot 94 defined by the two housing portions for receiving the cassette. A roller pump 96 is positioned near the rear end of the slot, the rollers of which bear against the aspiration tube 44 as they travel along the race 54. A pair of stop pins 97 (FIGS. 1 and 8) extending from the top housing 92 maintain the cassette 10 a precise distance from the rollers of the roller pump.

An aspiration solenoid 98, an irrigation solenoid 100, a support 102, and a twelve volt D.C. motor 104 are all mounted to the top housing. A valve assembly 106 is mounted to the support while a tube 108, shown in part in FIG. 8, is connected between the valve manifold assembly 110 and the aspiration solenoid 98. A vacuum sensor (not shown) is also connected to the valve manifold assembly.

The aspiration solenoid 98 includes a hollow plunger 112 having a suction cup 114 mounted to the bottom end thereof. The suction cup is positioned either directly over or upon the top surface of the cassette so that the passage 116 therein is in fluid communication with passage 64 when the cup is in the latter position.

The irrigation solenoid is used for controlling the passage of irrigation fluid through the irrigation tube 16. When the plunger 118 thereof is caused to move downwardly towards the cassette, the tip thereof enters the circular notch 18 and pinches the tube between itself and narrow ridge 20. A spring assembly 120 is provided for urging the plunger 118 towards the upper position so that irrigation fluid will continue to be supplied if the unit fails.

In operation, the cassette 10 is inserted within the slot 94 such that the flanges 68 thereof urge the fingers 81 of the cams 72, 74 rearwardly. This causes the cams to rotate about the shafts 76. Once the overcenter springs 84 have crossed the axes of the respective shafts 76, the cams will continue to rotate. The motion of the cassette will continue until the front face of the cassette engages the stop pins located in the top cover. This movement of the cams, which takes place automatically once the cassette is partially inserted, causes the cassette to be pushed by the cams into the proper position as the cam surfaces 81′ trailing the fingers 81 engage the flanges 68. The aspiration tube 44 accordingly bears against the rollers of the roller pump 96, the aspiration opening 65 is positioned beneath the suction cup 114, and the circular notch 18 is positioned beneath the plunger tip of the irrigation solenoid 100. The pins 97 and springs 84 insure that the cassette 10 is maintained in a substantially fixed position relative to the roller pump in order to provide consistent and reliable aspiration. The springs exert sufficient force to prevent the cassette from moving as the pump rollers bear against the aspiration tube 44. As discussed above, the phototransistor 89 allows the system to be operated when the cam 74 has been rotated to the operating position. The cassette is precluded from moving with respect to the pump rollers during the operation of the roller pump.

Irrigation is provided to the patient when the plunger 118 of the irrigation solenoid is in the raised position. Actuation of the solenoid causes the plunger to descend, thereby pinching the irrigation tube 16 between the plunger tip and the narrow ridge 20 within notch 18.

The surgery situs may be aspirated by causing the plunger 112 of the aspiration solenoid to descend. The suction cup 114 is thereby pushed into sealing engagement with the smooth upper surface of the cassette housing 12. Fluid and macerated tissue travel through tubes 52, 50 and 44, respectively, and out through the bottom of the cassette. The hydrophobic filter 58 prevents the fluid and tissue from traveling into passages 62, 64, 116 and to the vacuum sensor (not shown).

The roller pump causes the fluid and tissue to move through the tube 44 by peristaltic action in the direction shown by the arrow in FIG. 1. Although the rollers tend to pull the tube 44 in the direction of the arrow, the positioning of the tube within the slot 56 prevents it from assuming an excessively elliptical shape which would decrease the area through which the aspirated materials could flow. The upper and lower surfaces of the slot prevent the height of the tube from changing significantly, thereby preventing it from flattening when pulled against the portion of the cassette housing which defines the race 54. The aspiration process accordingly will proceed without interruption.

Once the operation has been completed, the voltage to the irrigation solenoid is discontinued to allow the plunger 118 to be moved to a raised position. The plunger 112 within the aspiration solenoid 98 is also moved to the raised position by energizing the aspiration solenoid. The cassette is then withdrawn from the slot 94 as the cams 72, 74 rotate back to the initial position by virtue of the cassette withdrawal process.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A cassette for an ophthalmic surgery system or the like, comprising:
    a channel extending through at least a portion of said housing and adjoining said race; and
    a slot defined by said housing at the junction of said channel and said race, said slot being defined by an upper surface, a lower surface and an inner surface extending substantially perpendicularly with respect to said upper and lower surfaces and connecting said upper and lower surfaces.

2. A cassette as defined in claim including a flexible tube positioned within said channel and extending adjacent to said race, said tube being positioned within said slot.

3. A cassette as defined in claim 2 wherein the height of said slot is less than the outside diameter of said flexible tube.

4. A cassette as defined in claim 2 wherein said channel has a generally Y-shaped configuration including three end portions, a first of said end portions adjoining a first end of said race, a second of said end portions adjoining a second end of said race, a first opening within said housing, a third of said end portions of said channel adjoining said opening.

5. A cassette as defined in claim 2 including a second channel extending through said housing, a narrow ridge extending across said channel, and a flexible irrigation tube positioned within said channel and passing over said narrow ridge.

6. A cassette as defined in claim 1 wherein said housing is of integral construction.

7. A cassette as defined in claim 2 wherein said cassette is substantially rectangular in cross section and includes a top surface, a bottom surface, a front end, a rear end, and a pair of sides, said race defining at least a portion of said rear end of said cassette.

8. A cassette as defined in claim 7 wherein said channel extends within said top surface of said housing.

9. A cassette as defined in claim 6 including a second channel within said housing, said second channel including an end adjoining said front end and a ridge extending thereacross, and an irrigation tube positioned within said second channel and passing over said ridge.

10. A cassette receptacle assembly for an opthalmic surgery irrigation/aspiration system comprising:
    a housing;
    a slot defined within said housing, said slot having a front end and a rear end;
    latching means mounted to said housing, said latching means including cassette engagement means for engaging a cassette inserted within said slot;
    a roller pump mounted to said housing, said roller pump including rollers positioned adjacent said rear end of said slot;
    spring means connected between said housing and said latching means for urging said latching means in a selected direction once said cassette engagement means have engaged a cassette, whereby said cassette is urged to a predetermined position with respect to a said roller pump; and
    means for maintaining a cassette in a substantially fixed, predetermined position with respect to said roller pump during the operation of said roller pump.

11. An assembly as defined in claim 10 wherein said latching means includes a pair of opposing cams, each of said cams including a finger extending within said slot.

12. An assembly as defined in claim 11 including a pair of shafts mounted to said housing, said cams being respectively rotatably mounted to said shafts.

13. An assembly as defined in claim 12 wherein said spring means include a first spring connected between said housing and one of said pair of cams for urging said one of said cams to rotate about the axis of one of said pair of shafts, and a second spring connected between said housing and the other of said pair of cams for urging said other cam to rotate about the axis of the other of said pair of shafts.

14. An assembly as defined in claim 10 including stop means extending from said housing and into said slot for engaging a cassette inserted within said slot a selected distance from said rollers of said roller pump.

15. An assembly as defined in claim 14 wherein said spring means and said stop means constitute said means for maintaining a cassette in a substantially fixed, predetermined position, said spring means having sufficient strength to overcome the force of said rollers against said cassette when said roller pump is operated.

* * * * *

UNITED STATES PATENT AND TRADEMARK OFFICE
CERTIFICATE OF CORRECTION

PATENT NO. : 4,904,168

DATED : February 27, 1990

INVENTOR(S) : Robert Cavoto et al.

It is certified that error appears in the above-identified patent and that said Letters Patent is hereby corrected as shown below:

Column 5, Claim 1, third line of claim 1 is missing.
before line 24, insert line reading:
--a housing including an arcuate race;--

Signed and Sealed this

Twenty-third Day of April, 1991

*Attest:*

HARRY F. MANBECK, JR.

*Attesting Officer*     Commissioner of Patents and Trademarks